United States Patent [19]

Mendel et al.

[11] Patent Number: 4,863,157
[45] Date of Patent: Sep. 5, 1989

[54] METHOD AND APPARATUS FOR EXERCISING A PARALYZED LIMB

[75] Inventors: Frank C. Mendel; Dale R. Fish, both of Tonawanda; William Tanski, Jr., Elma; Robert E. Kell, East Aurora, all of N.Y.

[73] Assignee: State University of New York, Albany, N.Y.

[21] Appl. No.: 187,746

[22] Filed: Apr. 29, 1988

[51] Int. Cl.⁴ .................. A63B 21/00; A63B 23/04; A63B 69/16

[52] U.S. Cl. ........................ 272/73; 272/DIG. 6; 128/24.1; 128/25 R; 128/25 B; 128/421; 623/25; 280/250.1; 280/252; 280/255

[58] Field of Search ............... 128/24.1, 24 R, 25 R, 128/25 B, 421; 272/73, DIG. 6; 623/25; 280/255, 252, 242 WC

[56] References Cited

U.S. PATENT DOCUMENTS

| | | | |
|---|---|---|---|
| 3,216,722 | 11/1965 | Odom | 128/25 R |
| 3,722,005 | 3/1973 | Cowland | 623/25 |
| 4,402,502 | 9/1983 | Peters | 128/25 R X |
| 4,421,336 | 12/1983 | Petrofsky et al. | 128/421 X |
| 4,523,769 | 6/1985 | Glaser et al. | 280/252 |
| 4,572,501 | 2/1986 | Durham et al. | 128/25 R X |
| 4,582,049 | 4/1986 | Ylvisaker | 128/24.1 |
| 4,586,495 | 5/1986 | Petrofsky | 128/25 B X |
| 4,612,924 | 9/1986 | Borkan | 128/421 |
| 4,705,269 | 11/1987 | DeBoer et al. | 272/73 |
| 4,811,964 | 3/1989 | Horn | 280/250.1 |

FOREIGN PATENT DOCUMENTS 1140181  1/1983  Canada ................ 280/242 R

OTHER PUBLICATIONS

Petrofsky et al., Bicycle Ergometer for Paralyzed Muscle, vol. 9, No. 1, Journal of Clinical Engineering, p. 13-19, (Jan.-Mar. 1984).

Primary Examiner—Richard J. Apley
Assistant Examiner—Joe H. Cheng
Attorney, Agent, or Firm—Robert P. Simpson; Michael L. Dunn

[57] ABSTRACT

A method and apparatus are provided for inducing contraction of a paralyzed muscle in a limb. The invention includes a method for providing electrical stimulation to a paralyzed limb in response to continuous motion of an uninvolved, or unparalyzed limb, as well as an apparatus to implement the method. A method and apparatus are also provided for transporting a person having a paralyzed limb. The transporting apparatus is propelled at least in part by the paralyzed limb which is induced to move by electrical stimulation of a paralyzed muscle in response to continuous motion of an uninvolved limb.

43 Claims, 5 Drawing Sheets

METHOD AND APPARATUS FOR EXERCISING A PARALYZED LIMB

BACKGROUND OF THE INVENTION

The present invention relates to a method and apparatus for inducing contraction of paralyzed muscles of a limb and also to a method and apparatus for transporting a person having a paralyzed limb by using the afflicted limb to power or propel the apparatus.

A growing number of persons with spinal cord injuries and other central nervous system disorders are receiving electrically-induced exercises as a part of their clinical rehabilitation program. When injury occurs to the spinal cord, neurons that connect the brain with lower motor neurons are often damaged. Alpha motor neurons below the level of the lesion remain healthy, even though communication from brain to alpha motor neurons is lost. In the absence of such communication, muscle groups in the paralyzed limb become debilitated through a process known as disuse atrophy. Continued muscle disuse results in adverse effects upon the heart and cardiovascular system, reduces blood volume, demineralizes bones, and causes muscle atrophy. Petrofsky, Phillips, Heaton and Glaser, *Bicycle Ergometer for Paralyzed Muscle*, 9:1 Journal of Clinical Engineering 13 (Mar., 1984).

Functional electrical stimulation of debilitated muscles has been demonstrated to improve the physical capacities of individuals with damage to their central nervous systems. Debilitated muscles can be restored to near normal function by electrical stimulation. Indeed, limited numbers of these individuals can now stand for long periods, power tricycles, and even walk with the aid of such stimulation.

Heretofore, apparatus utilized to evoke movement of paralyzed limbs have either used uninvolved i.e., unparalyzed, limbs (without electrical stimulation of paralyzed limbs) or have electrically stimulated paralyzed limbs without requiring concurrent exercise of uninvolved limbs. For example, a stationary patient-initiated response device and method for reeducating debilitated muscle tissue is disclosed in U.S. Pat. No. 4,582,049, issued Apr. 15, 1986, to Ylvisaker. This device is stationary and requires the use of hands only to operate switches, which trigger stimulation of the paralyzed limbs. A wheelchair powered by electrically stimulated paralyzed limbs is disclosed in U.S. Pat. No. 4,523,769, issued June 18, 1985 to Glaser et al. But, this device requires only the momentary manual operation of electrical switches to initiate stimulation of paralyzed limbs, i.e., uninvolved upper limbs are only minimally involved in the operation of this device. Indeed, switches operated by any uninvolved body part would suffice in initiating stimulation of paralyzed limbs in this wheelchair. In another device, an on-board computer is used to control electrical stimulation of paralyzed lower limbs of adults to propel a tricycle, as described by Petrofsky, Phillips, Heaton and Glaser, Bicycle Ergometer for Paralyzed Muscle, supra. This device requires no exercise of uninvolved limbs to initiate electrical stimulation of paralyzed lower limbs, i.e., electrical stimulation is fully computer-controlled. Dependence on a computer system (including stimulator and electrodes) and paralyzed limbs to propel this vehicle put the user at risk of being stranded if computer malfunction or fatigue of paralyzed limbs occurs.

SUMMARY OF THE INVENTION

The invention provides a method and apparatus for inducing contraction of a paralyzed muscle in a limb. The apparatus includes means for electrical stimulation of a paralyzed limb and means for actuating the stimulation means in response to continuous motion of an uninvolved limb. The invention further provides a method and apparatus for transporting a person having a paralyzed limb. The transporting apparatus includes means for electrical stimulation of a paralyzed limb, means for actuating the stimulation means in response to continuous motion of an uninvolved limb, and means for propelling the apparatus using a paralyzed limb.

Accordingly, it is an object of the present invention to provide a novel method and apparatus for inducing muscle contraction in a paralyzed or paretic limb and for transporting a person having a paralyzed or paretic limb using the paralyzed limb to propel the apparatus.

A more particular object of the invention is to provide a method and apparatus for inducing contraction of a paralyzed muscle in a paralyzed limb via electrical stimulation, wherein the paralyzed limb is stimulatd in response to continuous motion of an uninvolved limb.

Still another object of the invention is to provide a method and apparatus for transporting a person having a paralyzed limb where the paralyzed limb provides propulsion force and where the rate of travel of the apparatus is related to the rate of movement of an uninvolved limb and is not dependent upon a computer or other artificial timing device.

A further object of the invention is to provide an apparatus as described above that is especially adapted for use by children and which children will enjoy using.

Yet another object of the invention is to provide a transportation device as described above that further includes safety mechanism to prevent overstimulation of paralyzed limbs and to prohibit stimulation when the drive mechanism is stopped or in reverse.

Still a further object of the invention is to provide an apparatus as described above that is psychologically and physiologically beneficial to a person having a paralyzed limb.

Finally, the simple device that we describe herein is unique in that it combines motion of the uninvolved limbs and electrical stimulation of paralyzed limbs. Specifically, motion of the uninvolved limbs controls electrical stimulation of paralyzed limbs, therefore, stimulation is independent of computers or other artificial timing devices, i.e., the user continually determines rate of movement. Further, even early in the rehabilitation process, a user can propel the vehicle entirely by the uninvolved limbs: at no time would malfunction of the electrical stimulation system render the vehicle useless. Also unique is the adaptation of the device described herein for use by children with paralyzed limbs.

These and further features, objects and advantages of the invention will become apparent to those skilled in the art from the following detailed description and appended drawings.

DETAILED DESCRIPTION OF THE INVENTION

Figure 1:
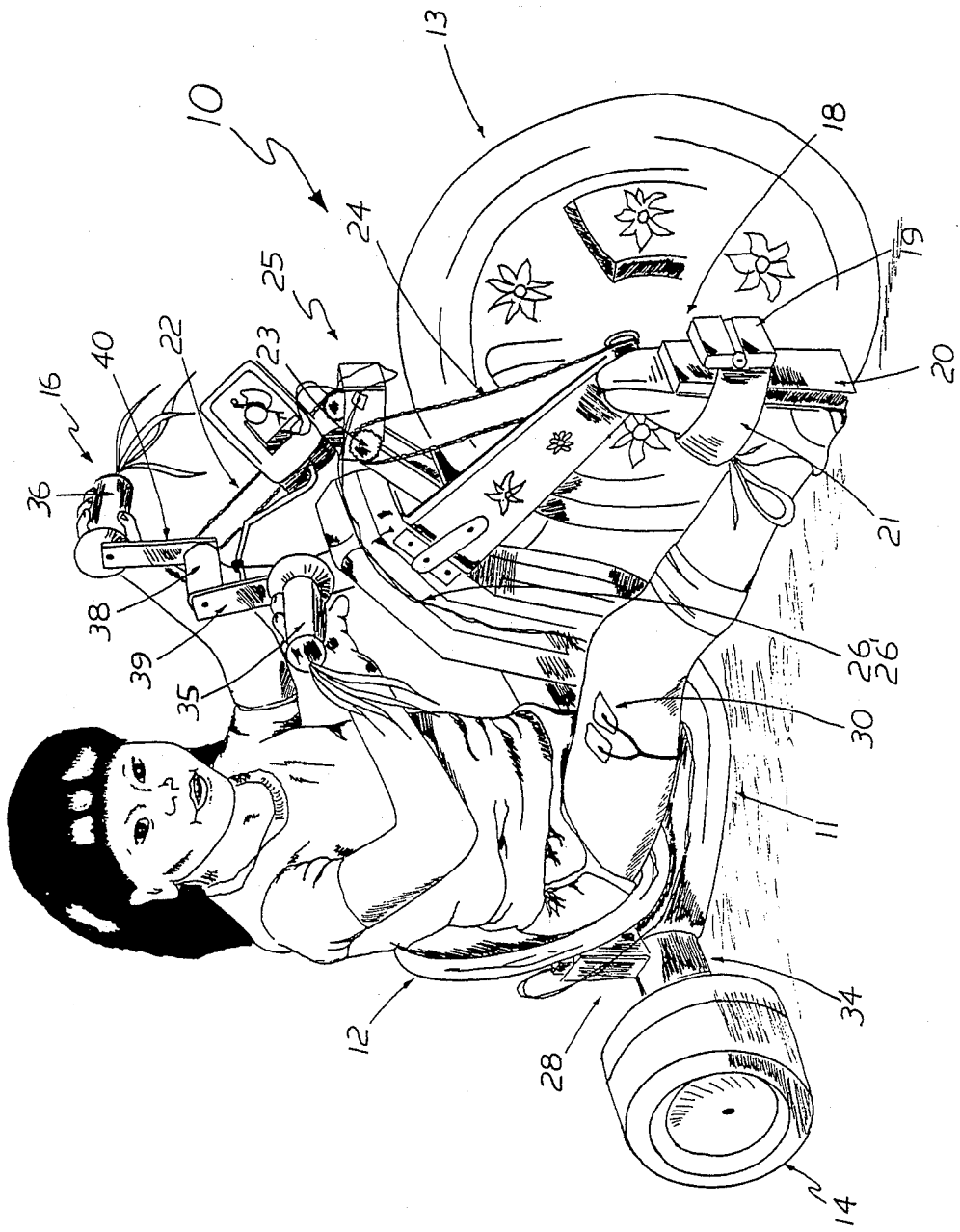
FIG. 1 is a side perspective view of a first embodiment of the invention.

At the outset, it should be clearly understood that the drawings are to be read together with the specification, and are to be considered a portion of the entire "written description" of this invention, as required by 35 U.S.C. 112. Also, identical reference numerals on different figures refer to identical elements of the invention.

The essence of the invention, as demonstrated by the claims, is a method and apparatus for providing electrical stimulation to paralyzed or paretic muscles in response to continuous motion of an uninvolved limb. The invention also provides a method and apparatus for transporting a person having a paralyzed limb by providing electrical stimulation to paralyzed or paretic muscles in response to continous motion of an uninvolved limb. The transportation apparatus utilizes the paralyzed limb for propulsion.

For purposes of this description, a paralyzed limb is one having either paralyzed or paretic muscles. A paralyzed muscle does not respond effectively to volitional effort because the pathway from brain to lower motor neurons has been interrupted. A paretic muscle is one that is only partially paralyzed. An uninvolved limb is one having completely, or substantially all normal, unparalyzed muscles. Also for purposes of this description, "continuous motion" is defined to mean sustained motion or movement of an uninvolved limb. Examples of continuous motion include turning a handcrank or footcrank. The motion may take any shape or form; it may be rotary motion or reciprocating motion; it may be synchronized or unsynchronized; it may be coordinated or uncoordinated with associated motion of the paralyzed limb. Continuous motion is not, however, momentary, one-shot, unsustained movement such as depressing a switch, pushing a lever, turning a knob, etc. To be continuous, the motion must be sustained. It cannot be of short duration.

It should also be understood that, whereas a first embodiment is shown in the form of an improved tricycle, the scope of the claimed invention is not limited to a tricycle embodiment. The aspect of the invention relating only to inducement of muscular contraction of paralyzed muscles, without means for transportation, obviously need not take the form of a tricycle. Any apparatus that provides electrical stimulation of a paralyzed limb in response to continuous motion of an uninvolved limb is intended to be within the scope of the claims. Similarly, the transportation aspect of the invention may take many forms. For example, one such embodiment is a wheelchair, wherein a paraplegic would turn a handcrank with uninvolved upper limbs, and electrical stimulation of paralyzed lower limbs would occur in response to the continuous motion of the upper limbs. The lower limbs would then be operatively arranged to propel the wheelchair.

FIG. 1 illustrates a side perspective view of the first embodiment of the invention. For purposes of illustration, safety features such as chain guards and covers for mechanical linkages have been omitted. Improved tricycle 10 includes frame 11, seat 12 mounted on frame 11, front wheel 13 rotatably mounted on frame 11, right rear wheel 14 and left rear wheel 15 (shown in FIG. 2) secured to common rear axle 34, which is rotatably mounted on frame 11, hand crank 16, which is rotatably mounted on frame 11, and foot crank 18, which is also rotatably mounted on frame 11. As in a typical tricycle, foot crank 18 is mechanically linked to front wheel 13. Right pedal 19 of foot crank 18 has been modified to accommodate the foot of a paralyzed limb. Foot support 20 and foot strap 21 function to secure the foot of a paralyzed leg to pedal 19.

Unlike a typical tricycle, tricycle 10 includes hand crank 16 instead of standard handlebars. Hand crank 16 is pivotally mounted to frame 11 and mechanically linked to front wheel 13 for the purpose of steering the tricycle. Pulling back on right hand grip 35 will cause front wheel 13 to turn right whereas pulling back on left hand grip 36 will cause front wheel 13 to turn left. Hand grips 35 and 36, which include a mechanism to sense whether or not hands are in position on the grips (discussed infra), are secured to hand crank axle 38 by support arms 39 and 40, respectively. Hand grips 35 and 36 are arranged for rotation about axle 38. Axle 38 is rotatably mounted to frame 11. Hand chain 22 links hand crank axle 38 to control axle 23. Thus it is seen that rotating hand crank 16 causes front wheel 13 and foot crank 18 to rotate.

As in a normal tricycle, right pedal 19 is displaced 180 degrees relative to left pedal (not shown). Similarly, left hand grip 36 is displaced 180 degrees relative to right hand grip 35. Moreover, in a first embodiment depicted in FIG. 1, a one-to-one correspondence exists between the position of hand grips 35 and 36, the right and left pedals, respectively. One complete revolution of hand crank 16 corresponds exactly to one complete revolution of foot crank 18. When hand grip 35 is positioned closest to the ground, so also is pedal 19, etc. This one-to-one correspondence between the motion of the paralyzed and uninvolved limb is merely illustrative, and is not intended as a critical limitation of the invention.

Figure 2:
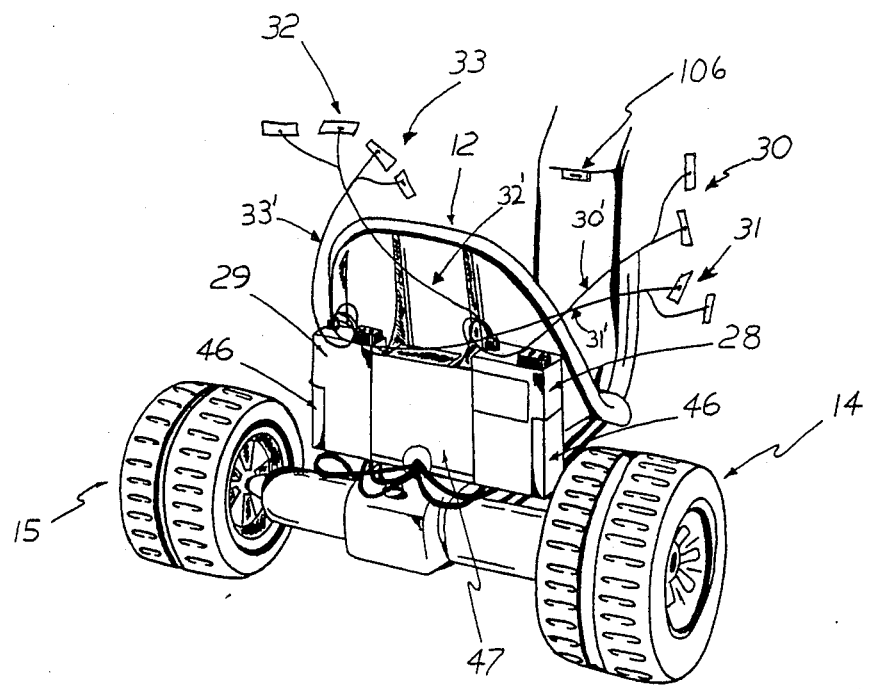
FIG. 2 is a sectional rear perspective view of the embodiment depicted in FIG. 1.

Sensing means 25 functions to sense the position of hand crank 16, and generates position signals, which are communicated via electrical conductors 26 and 26' to stimulating means 28 and 29 (shown in FIG. 2). Stimulating means 28 and 29 are electrostimulators. As shown in FIGS. 1 and 2, depending on the position of hand crank 16 as indicated by sensing means 25, stimulating means 28 generates neuromuscular stimulation signals to electrode pairs 30 and 32, via electrical conductors 30' and 32', respectively. Similarly, stimulating means 29 generates neuromuscular stimulation signals to electrode pairs 31 and 33, via electrical conductors 31'and 33', respectively. Electrode pairs 30, 31, 32 and 33 are shown as surface electrodes, but implantable electrodes (not shown) would perform the same function. The above mentioned electrodes are positioned over predetermined muscle groups. In a first embodiment depicted in FIG. 1, stimulating means 28 transmits neuromuscular stimulation signals to electrode pairs 30 and 32, which are placed over right quadriceps and left adductors, respectively. Stimulating means 29 transmits neuromuscular stimulating signals to electrode pairs 31 and 33, which are placed over right adductors and left quadriceps, respectively. As right hand grip 35 and pedal 19 reach zenith, stimulating means 28 transmits neuromuscular stimulation signals to electrode pairs 30 and 32 overlying right quadriceps and left adductors, respectively. Right quadriceps straighten the right knee and thus rotate wheel 13 clockwise. Simultaneously, left adductors are stimulated to prevent left knee from falling outward as left knee bends. Similarly, as left hand grip 36 and the left pedal reach zenith, stimulating means 29 transmits neuromuscular stimulation signals to electrode pairs 31 and 33 overlying right adductors and left quadriceps, respectively, and thereby produce muscular contractions that prevent right knee falling outward and rotate wheel 13 clockwise. Selection of these muscles is merely illustrative, and is not intended as a critical limitation of the invention. Indeed, the number of muscles stimulated in a first embodiment is fewer than the number desired.

The neuromuscular signals stimulate the paralyzed muscles to contract, thereby causing movement of the paralyzed limb in response to continuous motion of the uninvolved limb, which turns the hand crank. Thus, it is seen that tricycle 10 is propelled by a paralyzed limb.

Tricycle 10 may be adapted for stationary use by placing a stationary adapter under front wheel 13. Such an adapter is placed on a floor and contains rolling means, which engage front wheel 13, thereby allowing the apparatus to be used in the confines of a room, for example. In a first embodiment shown in FIG. 1, however, tricycle 10 transports the user from place to place using the user's paralyzed limb as a source of propulsion. The rate of inducement of the paralyzed muscles of the afflicted limb is related to the rate of motion of the uninvolved limb, and is proportional thereto. Thus, a small child can easily learn that faster movement of the hand crank will result in a faster rate of stimulation to the paralyzed limb and will result in a faster rate of travel of the tricycle. Similarly, a slower rate of movement of the hand crank results in a slower stimulation rate and slower speed of the tricycle. The rate of stimulation is directly controlled by the user.

The tricycle shown in FIG. 1 includes several safety mechanisms to prevent injury to the user. First, master power on-off switch 106 (shown in FIG. 2) is provided on frame 11 within easy reach of the user. This switch must be closed to energize stimulators 28 and 29. Opening this master on-off switch immediately interrupts power to the stimulators, thus obviating stimulation.

Figure 4:
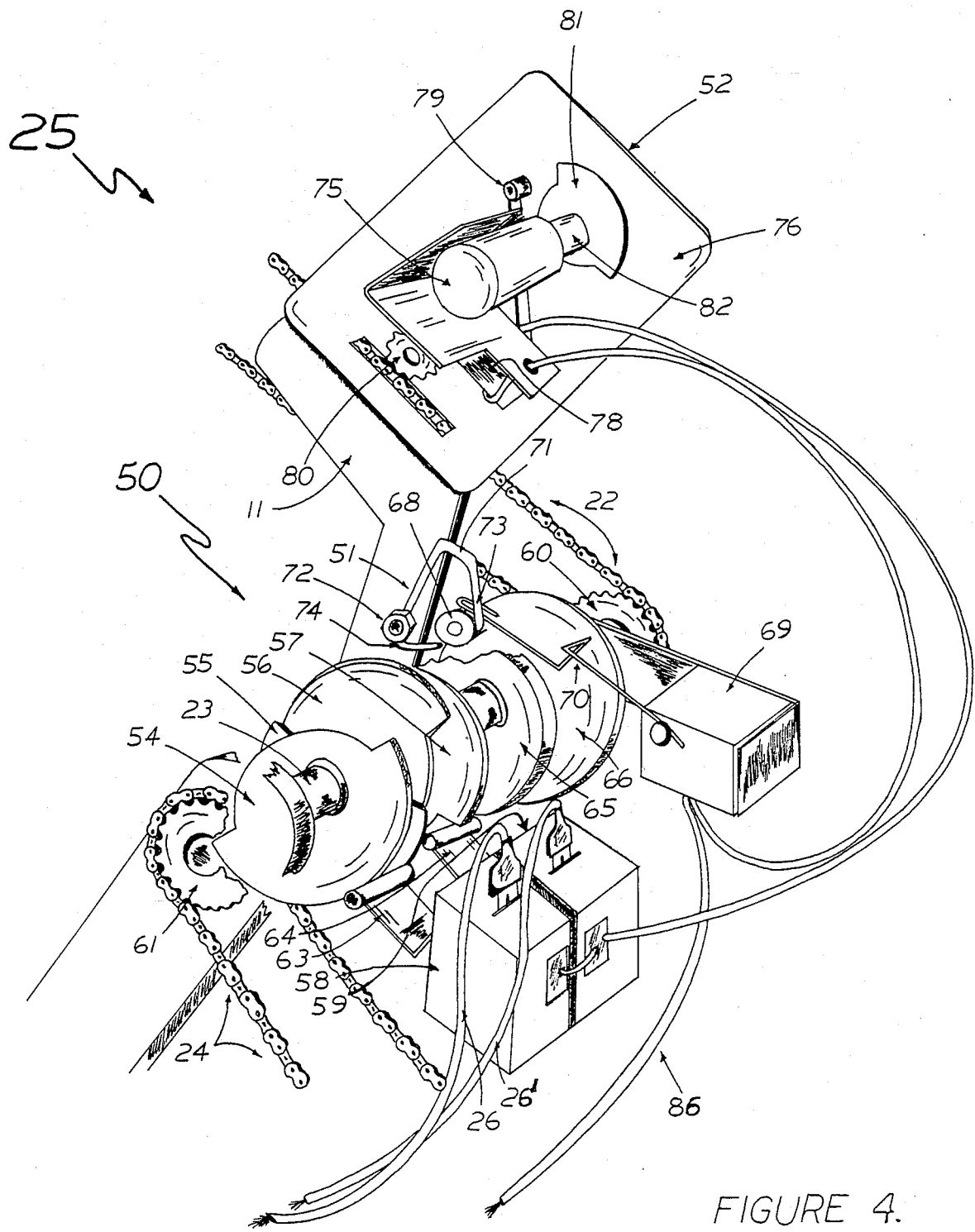
FIG. 4 is an enlarged view of the sensing means aspect of the embodiment shown in FIG. 1.

Not shown in the drawings is a motion detector means, which ensures that stimulation will occur only when front wheel 13 is in motion. This safety device includes a standard bicycle generator mounted on the front wheel fork. The rotor of this generator engages front wheel 13 such that rotation of wheel 13 causes rotation of the rotor and thereby generates a voltage. This voltage output controls a relay, which also functions to interrupt or connect main power to stimulators 28 and 29. This safety device ensures that power will only be supplied when front wheel 13 is in motion. If, for example, the tricycle engages an abutment preventing forward motion, power will immediately be disconnected from the stimulators. Sensing means 25 includes a forward motion safety means 51 (as shown in FIG. 4), which disconnects power to electrostimulators 28 and 29 if the user turns hand crank 16 in reverse. Sensing means 25 also includes an overstimulation control means 52, which permits supply of power to electrostimulators for a certain number of revolutions of the hand crank and then disrupts power for a predetermined further number of revolutions. The number of revolutions with and without power can be varied by changing the cam to accommodate changes in endurance of paralyzed muscles. Also, to ensure that stimulation is received by the paralyzed limb only during the time that an uninvolved limb is in continuous motion, hand grips 35 and 36 are equipped with means for sensing that the user's hands are in place on the grips. Should the hands break contact with the grips, power is immediately disconnected from the electrostimulators.

FIG. 2 depicts a rear perspective view of tricycle 10. Storage compartment 46 contains electrostimulators 28 and 29, and rechargeable battery pack 47. Electrostimulators 28 and 29 may be any neurostimulator capable of stimulating paralyzed or paretic muscles. In a first embodiment, Respond II neurostimulators, available from Medtronic, Inc., Minneapolis, Minnesota, are used successfully. The Respond II units are constant current generators that provide biphasic rectangular waveforms of 300 microsecond duration. These units are adjusted to further provide stimuli at 50Hz, at intensities up to 90 mA and set to deliver continuous pulse trains. Sensing means 25 directs power supply to the stimulators and thus converts continuous pulse trains to intermittent sequences.

Figure 3:
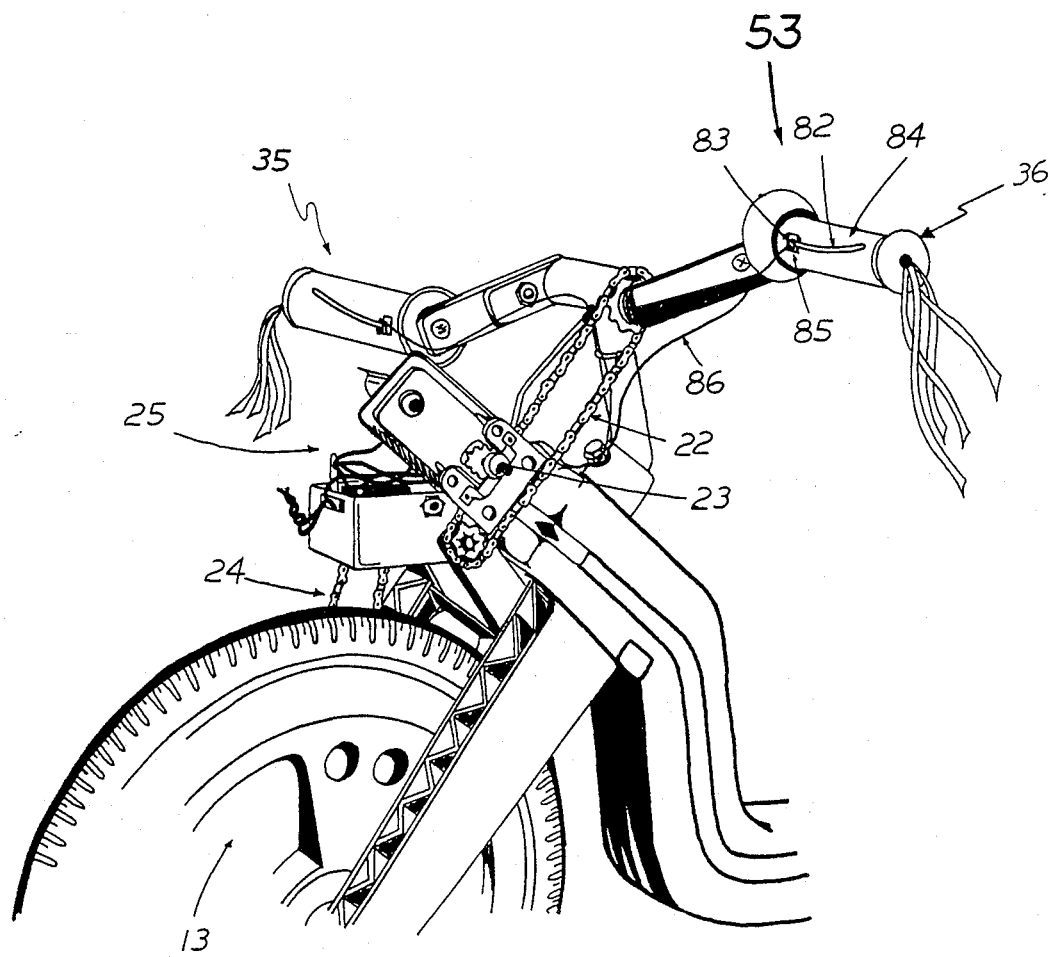
FIG. 3 is a sectional side perspective view of the hand crank and chain-driven control assembly of the embodiment depicted in FIG. 1.

FIG. 4 is an enlarged view of sensing means 25. Sensing means 25 includes stimulation control means 50, motion detector means (not shown), forward motion safety means 51, overstimulation control means 52, and hand grip sensing means 53 (FIG. 3). Stimulation control means 50 includes control axle 23, control cams 54, 55, 56 and 57 mounted on control axle 23, and cam-activated power distribution switches 58 and 59. Hand crank chain 22 engages sprocket 60, which is secured to one end of control axle 23. Foot crank chain 24 engages sprocket 61, which is secured to the other end of control axle 23. Thus, it is seen that rotation of hand crank 16 causes rotation of control axle 23 and cams 54–57. Cams 54 and 55 control power distribution switch 58 whereas cams 56 and 57 control power distribution switch 59. Switch 58 controls power to right stimulator 28 and switch 59 controls power to left stimulator 29 via stimulator power lines 26 and 26', respectively. As shown in FIG. 4, cams 54 and 56 are diametrically opposed in orientation on control axle 23, and cams 55 and 57 are similarly diametrically opposed in orientation. Switch 58 completes the power circuit to stimulator 28 when switch lever 63 is pushed downwardly by cams 54 or 55 and interrupts power to stimulator 28 when cam 54 or 55 allows switch lever 63 to spring upwardly. Similarly, switch 59 completes the power circuit to stimulator 29 when switch lever 64 is pushed downwardly by cam 56 or 57 and interrupts power to stimulator 29 when cam 56 or 57 allows switch lever 64 to spring upwardly. Thus, cams 54–57 provide signals for selectively energizing stimulators 28 and 29 dependent upon the position of common axle 23, which in turn depends upon the position of hand crank 16.

Forward motion safety means 51 includes annular disk magnet 65, which is secured to rotate with control axle 23, slip ring 66, which freely rotates about control axle 23, disk 68 secured to slip ring 66, which in turn is magnetically coupled to magnet 65, forward motion safety switch 69 having switch lever 70, and detente 71 mounted to frame 11 by bolt 72 and having forward member 73 and reverse member 74. As control axle 23 rotates in a clockwise direction, corresponding to forward movement of tricycle 10, magnet 65 also rotates in a clockwise direction, inducing disk 68 and slip ring 66 to rotate in a clockwise direction. Disk 68 engages lever 70, pushing the lever upward to close forward safety switch 69, which allows power to be delivered to stimulators 28 and 29. Forward member 73 of detente 71 engages disk 68 and prevents it from further clockwise rotation. When hand crank 16 is turned in a counter-clockwise rotation so as to turn control axle 23 in a counter-clockwise direction, magnet 65 also rotates in a counter-clockwise direction, inducing disk 68 and slip ring 66 to also rotate counter-clockwise. As disk 68 rotates counter-clockwise, it disengages lever 70, allowing it to fall, thereby opening forward motion safety switch 69 and interrupting power to stimulators 28 and 29. Reverse member 74 of detente 71 engages disk 68 and prevents it from further counter-clockwise rotation. Thus, forward motion safety means 51 functions to prevent power from being supplied to stimulators 28 and 29 when hand crank 16 is rotated counter-clockwise so as to propel tricycle 10 backwards.

Overstimulation control means 52 includes revolution counter 75 having axle 82, gearbox 76, microswitch 78 activated by lever 79, sprocket 80, and cam 81 secured to axle 82. As hand chain 22 moves, it engages sprocket 80 causing it to rotate. Sprocket 80 is linked through gearbox 76 to axle 82 of revolution counter 75. Gearbox 76 is arranged such that one complete revolution of axle 82 and cam 81 corresponds to sixty revolutions of hand crank 16. As cam 81 rotates, it engages lever 79 which closes microswitch 78, permitting power to stimulators 28 and 29. Cam 81 engages lever 79 for a time equivalent to thirty revolutions of hand crank 16. After thirty revolutions, cam 81 rotates to disengage lever 79 and open microswitch 78, disconnecting power from stimulators 28 and 29. Cams of different effective arcs may be substituted for cam 81 so that lever 79 is engaged for more or less than thirty revolutions. Thus, power is alternately supplied and disconnected at any predetermined number of revolutions, thereby preventing muscle fatigue due to overstimulation. Note that numbers of revolutions with stimulation need not be equal to number of revolutions without stimulation.

Although overstimulation protection means 52 is shown as a mechanical device, this means could alternatively comprise an electronic device. For example, electronic counters could be operatively arranged to sense the number of revolutions of hand-crank 16 and could be further arranged to supply power to electrostimulators 28 and 29. Electronic counters would have the advantage of flexibility, in that they could be pre-set to any specified rotation count merely by turning a dial. The counter would then automatically reset to 0 at each startup.

Handgrip sensing means 53 is also shown in FIG. 3. Both handgrips 35 and 36 include sensing means 53. Sensing means 53 comprises spring biased lever 82, which is pivotally mounted on handgrip 36 and functions to open and close microswitch 85. Spring 83 biases lever 82 into a position away from outer cylindrical surface 84 of handgrip 36. When lever 82 is in this position, microswitch 85 is open and power is disconnected from stimulators 28 and 29. When the hand of an uninvolved limb is in position on handgrip 36 so as to depress lever 82 toward surface 84, microswitch 85 is closed and power is supplied to stimulators 28 and 29 via line 86. Only one lever on either handgrip 35 or 36 need be depressed to provide power to stimulators 28 and 29. Thus, handgrip sensing means 53 functions to provide power to stimulators 28 and 29 only when a hand of an uninvolved limb is in position on one of the handgrips. Safety means 50, 51, 52, 53 and motion detector means (not shown) collectively function to ensure that stimulation of paralyzed limb occurs only when an uninvolved limb is in motion, front wheel 13 is rotating forward and the number of consecutive revolutions of cranks does not exceed a specified (but variable) number.

Figure 5:
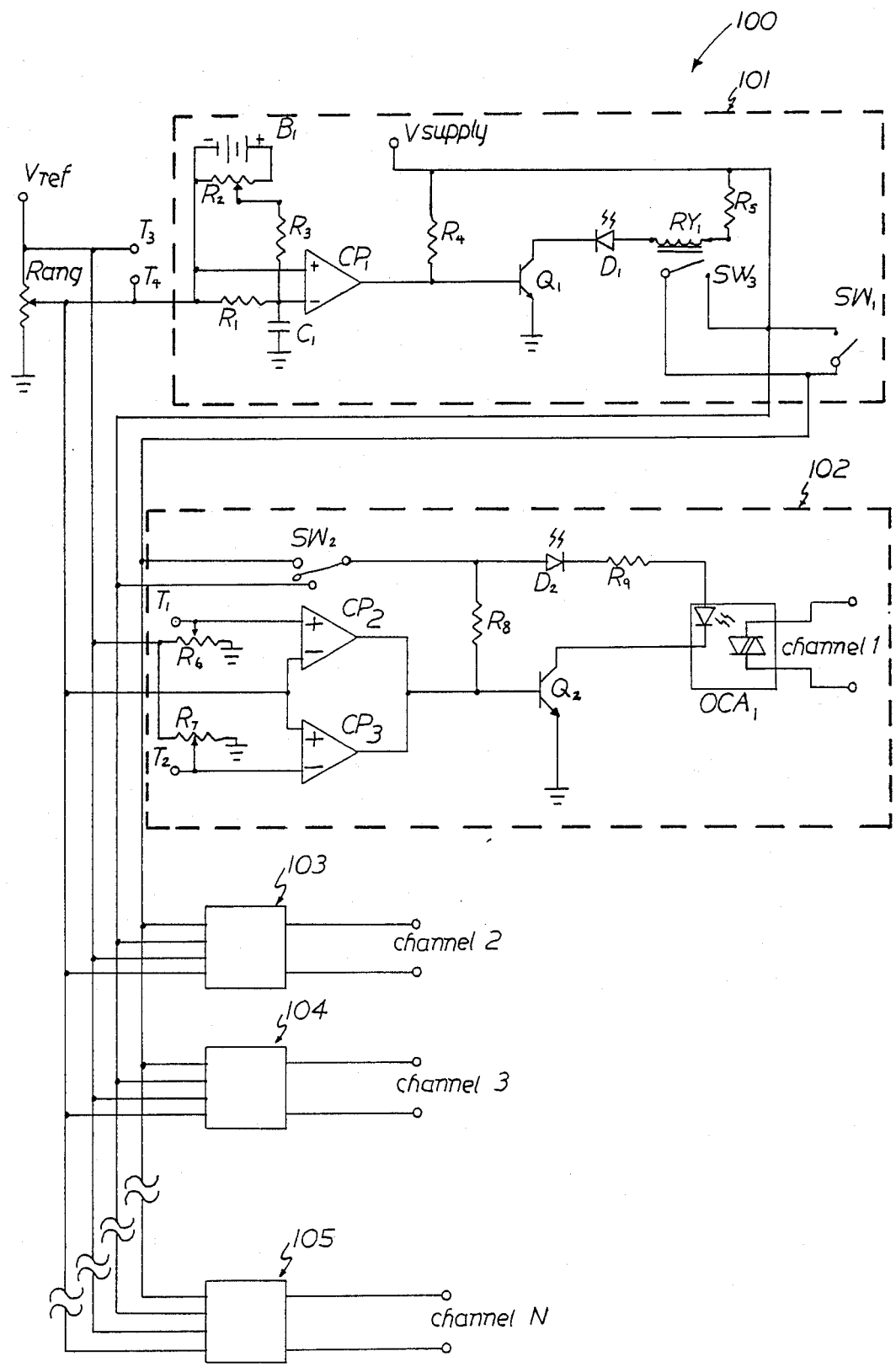
FIG. 5 is a schematic diagram of an alternative electronic sensing and safety means for the invention.

Alternatively, sensing means 25 and forward motion safety means 51 may comprise an electronic circuit and apparatus as shown in FIG. 5. A second embodiment of tricycle 10 includes these alternative sensing and safety means. Referring now to FIG. 5, circuit 100 comprises forward motion sensing circuit 101 and voltage-controlled switching circuits 102-105. Circuit 100 uses a single continuous-rotation potentiometer $R_{ang}$ as a goniometric device to control a plurality of independent stimulation channels 1, 2, 3, ..., N. Potentiometer $R_{ang}$ has a variable resistance $R_{position}$, which is a fraction of $R_{ang}$ and which corresponds to the rotational position of hand crank 16. Using simple voltage division, a voltage, $V_{position}$, which corresponds to the angular position of hand crank 16, is given by the formula, $$V_{position} = \frac{R_{position}}{R_{ang}} \times V_{REF}$$

Circuit 100 provides for the various channels to be turned on or off in sequence in synchronism with the rotation of hand crank 16. Circuit 100 permits independent adjustment of the angular position at which each stimulator channel is first turned on and the angular arc or rotational crank angle of hand crank 16 and potentiometer Rang over which it delivers stimulation pulses to the user.

A forward motion sensing feature is included to inhibit stimulation until the forward motion exceeds a preset threshold, to prevent unwanted stimulation when the user is at rest or is maneuvering in reverse. The basic elements of this device include: goniometric potentiometer $R_{ang}$ to provide a voltage proportional to hand crank angle, forward motion circuit 101, a plurality of voltage-controlled switching circuits 102-105, which respond to the angle-dependent voltage and close the appropriate switch to energize the corresponding stimulation channel. As shown in FIG. 5, switching circuit 102 is shown in detail and circuits 103-105 are each identical to circuit 102. Also shown in FIG. 5, the number of channels controlled by sensing circuit 100 is selectable. Forward motion sensing circuit 101, uses a single comparator $CP_1$ (for example as provided by one section of an LM339 quad comparator) together with RC differentiator ($R_1$ and $C_1$) to provide a voltage roughly proportional to the time derivative of the angle-sensed voltage. A small adjustable bias current is also applied to $R_1$ by the combination of auxiliary battery $B_1$ and potentiometer-resistor network $R_2$ and $R_3$. The bias level is set by $R_2$, whereas $R_3$ serves as a buffer to minimize load on $R_1$. This adjustable bias is used to set the minimum angular velocity at which comparator $CP_1$ will switch transistor $Q_1$ from nonconducting to conducting and actuate relay $RY_1$. When relay $RY_1$ is energized, switch $SW_3$ is closed, thereby connecting supply voltage to switching channels 102-105.

Focusing now on the switching channels 102-105, major components of each switching channel are as follows: window comparator range adjustment potentiometers, transistor amplifiers, optocoupler triacs, a three position single pole switch, an LED pilot light to indicate "status" of an individual channel, current limiting resistors, and pull-up resistors R4, R5, R8 and R9.

Referring now to switching current 102, window comparator comprising CP2 and CP3 operates with the two comparator outputs connected in parallel. For either unit alone, the output terminal is essentially grounded when the input differential voltage is positive. The negative input terminal of CP2 is connected to the positive terminal of CP3. The common junction between the inputs to CP2 and CP3 is used as the input to the window comparator. The positive terminal of CP2 is connected to the movable arm of window comparator range potentiometer R6, which provides a bias voltage representing the upper limit of the window. The negative terminal of CP3 is similarly connected to the movable arm of window comparator range potentiometer R7, which provides a bias voltage representing the lower limit of the window. The angle-sensed voltage, which comes from goniometric potentiometer $R_{ang}$ and is distributed via its own bus to the input of each window comparator, will increase linearly as hand crank 16 is rotated. When this voltage is less than bias level set by R7, the output terminal of CP3 is brought close to ground potential, which drives the base of transistor $Q_2$ to ground and cuts off its collector.

As the angle-sensed voltage increases, it will eventually exceed the bias set by R7, and the output terminal of comparator CP3 will no longer be forced to ground. If, at the same time, the bias applied to the positive terminal of CP2 is higher than the angle-sensed voltage, it too will permit its output to rise above ground. Because both outputs are connected in parallel, their common junction potential will rise above ground and allow the base voltage of transistor $Q_2$ to rise, allowing current through the collector-emitter circuit and actuating optocoupler $OCA_1$. This action also causes light emitting diode $D_2$ to glow, indicating that channel 1 is energized.

As the angle-sensed voltage continues to increase, it will at some point exceed the bias set by R6. At this point, and for any larger value of the input voltage, the differential voltage applied to CP2 will be negative, and its output will be forced to ground, bringing the base voltage of transistors $Q_2$ to ground and cutting off optocoupler $OCA_1$. Note that any current-actuated device, such as a relay, could be substituted for the optocoupler. The optocoupler was chosen for its low cost, low power consumption, and small size and weight.

Three-pole switch SW2 functions to allow individual channels to be switched to "on" (top position) in normal mode, with forward motion circuit 101 active; "off" (center position, as shown); or "on" (bottom position) independent of the state of forward motion circuit 101. This switch was included to allow setting the lower and upper limit potentiometers R6 and R7 relative to desired hand crank angles. Adjustment of these limits is facilitated by using a voltmeter on test point $T_1$ or $T_2$, while adjusting the associated potentiometer R6 or R7. As stated earlier, $V_{position}$ corresponds to the angular position of hand crank 16. $V_{position}$ is communicated to the junction of the negative input of CP2 and the positive input of CP3. Potentiometers R6 and R7 are set to values $R_{6set}$ and $R_{7set}$ to determine when channel 1 is activated. Using simple voltage division, the input voltage to the positive input of CP2 is given by the formula, $$V_{CP2} (R_{6set}/R_6) \times V_{REF}$$

and the input voltage $V_{CP3}$ to the negative input of CP3 is given by the formula, $$V_{CP3} = (R_{6set}/R_6) \times V_{REF}$$

Window comparator circuit 102 functions to control the on/off status of channel 1 as follows:

| Voltage Conditions | Channel Status |
| --- | --- |
| $V_{ang} < V_{CP3}$ | OFF |
| $V_{CP3} < V_{ang} < V_{CP2}$ | ON |
| $V_{ang} > V_{CP2}$ | OFF |

As hand crank 16 rotates, the setting of R6 and R7 determine the angular positions of the crank at which channel 1, turns on and off.

Thus, it is seen that the electronic embodiment of sensing means 25 and forward motion safety means 51 offers all the control and safety capabilities of the first embodiment and additionally provides for control of a virtually unlimited number of channels, independent control of the on/off times of each channel, and may allow for direct control of the stimulator electrode potential as opposed to control of the stimulator power source. This electronic circuit allows for time-sharing a single stimulator channel among a plurality of electrode pairs.

While the form of apparatus herein described constitutes a preferred embodiment of this invention, it is to be understood that the invention is not limited to this precise form of apparatus, and that changes may be made therein without departing from the scope of the invention; which is defined in the appended claims.

What is claimed is:

1. Apparatus for inducing muscle contraction in a paralyzed limb, comprising:
   means for electrical stimulation of said paralyzed limb; and
   means for actuating said stimulation means in response to continuous motion of an uninvolved limb.

2. Apparatus as recited in claim 1 wherein said means for actuating said stimulation means in response to continuous motion of an uninvolved limb comprises:
   moving means responsive to said uninvolved limb in motion; and
   means for sensing a position of said moving means and for providing a position signal indicative of said position.

3. Apparatus as recited in claim 2 wherein said means for electrical stimulation of said paralyzed lim comprises:
   processing means operatively arranged to receive and process said position signal and transmit a neuromuscular stimulation signal in response thereto; and
   a plurality of electrodes operatively arranged to receive said neuromuscular stimulation signal from said processing means and transmit said stimulation signal to predetermined paralyzed muscles to induce contraction of said paralyzed muscles of said paralyzed limb.

4. Apparatus as recited in claim 2 wherein said moving means is a mechanical crank.

5. Apparatus as recited in claim 2 wherein said means for sensing the position of said moving means and for providing a position signal indicative of said position comprises a mechanical cam sensing device.

6. Apparatus as recited in claim 2 wherein said means for sensing the position of said moving means and for providing a position signal indicative of said position comprises an electronic sensing device.

7. Apparatus as recited in claim 3 wherein said processing means comprises an electrostimulator.

8. Apparatus as recited in claim 3 wherein said plurality of electrodes are surface electrodes secured to skin surrounding said paralyzed limb.

9. Apparatus as recited in claim 3 wherein said plurality of electrodes are implantable electrodes.

10. Apparatus as recited in claim 1 wherein said means for electrical stimulation of said paralyzed limb provides said electrical stimulation at a rate which is related to the rate of continuous motion of said uninvolved limb.

11. Apparatus as recited in claim 1 wherein said means for electrical stimulation of said paralyzed limb provides said electrical stimulation at a rate which is proportional to the rate of continuous motion of said uninvolved limb.

12. Apparatus for inducing muscle contraction in a paralyzed limb, comprising:
means for electrical stimulation of said paralyzed limb; and
means for energizing said stimulation means only during a time that an uninvolved limb is in continuous motion.

13. Apparatus for inducing muscle contraction in a paralyzed limb, comprising:
means for electrical stimulation of said paralyzed limb; and
means for actuating said stimulation means only during a time that an uninvolved limb is in motion.

14. Apparatus for transporting a person having a paralyzed limb, comprising:
means for electrical stimulation of said paralyzed limb;
means for actuating said stimulation means in response to continuous motion of an uninvolved limb; and
means for propelling said apparatus using said paralyzed limb.

15. Apparatus as recited in claim 14 wherein said means for actuating said stimulation in response to continuous motion of an uninvolved limb comprises:
moving means responsive to said uninvolved limb in motion; and
means for sensing a position of said moving means and for providing a position signal indicative of said position.

16. Apparatus as recited in claim 14 wherein said means for propelling comprises a pedal-driven wheel rotatably mounted on said apparatus.

17. Apparatus as recited in claim 15 wherein said means for electrical stimulation of said paralyzed limb comprises:
processing means operatively arranged to receive and process said position signal and transmit a neuromuscular stimulation signal in response thereto; and
a plurality of electrodes operatively arranged to receive said neuromuscular stimulation signal from said processing means and transmit said stimulation signal to predetermined paralyzed muscles to induce contraction of said paralyzed muscles of said paralyzed limb.

18. Apparatus as recited in claim 15 wherein said moving means is a mechanical crank.

19. Apparatus as recited in claim 15 wherein said means for sensing position of said moving means and for providing a position signal indicative of said position comprises a mechanical cam sensing device.

20. Apparatus as recited in claim 15 wherein said means for sensing a position of said moving means and for transmitting a position signal indicative of said position comprises an electronic sensing device.

21. Apparatus as recited in claim 17 wherein said processing means comprises an electrostimulator.

22. Apparatus as recited in claim 17 wherein said plurality of electrodes are surface electrodes secured to the skin surrounding said paralyzed limb.

23. Apparatus as recited in claim 17 wherein said plurality of electrodes are implantable electrodes.

24. Apparatus as recited in claim 14 wherein the means for propelling said apparatus using said paralyzed limb functions to propel said apparatus at a rate which is related to the rate of motion of said uninvolved limb.

25. Apparatus as recited in claim 14 wherein the means for propelling said apparatus using said paralyzed limb functions to propel said apparatus at a rate which is proportional to the rate of motion of said uninvolved limb.

26. Apparatus for transporting a person having a paralyzed limb and an uninvolved limb wherein said apparatus is a tricycle having a frame, a pedal-driven front wheel rotatably mounted on said frame, a right rear wheel rotatably mounted on said frame, a left rear wheel rotatably mounted on said frame, and a seat secured to said frame, the improvement which comprises:
a hand-crank steering mechanism pivotably mounted on said frame and mechanically linked with said front wheel such that pivoting said mechanism in a clockwise direction causes said front wheel to turn right and pivoting said mechanism in a counterclockwise direction causes said front wheel to turn left, said hand-crank also operatively arranged for rotation and mechanically linked to said front wheel such that rotation of said hand-crank causes said front wheel to rotate to propel said tricycle;
sensing means for sensing a crank angle position of said hand-crank steering mechanism and for providing a position signal indicative of said position;
processing means for receiving said position signal and for transmitting a neuromuscular stimulation signal in response thereto;
a plurality of electrodes operatively arranged to receive said neuromuscular stimulation signal from said processing means and transmit said stimulation signal to a paralyzed muscle to induce contraction of said paralyzed muscle of said paralyzed limb, wherein said paralyzed limb powers said pedal-driven front wheel.

27. A method for inducing muscle contraction in a paralyzed limb, comprising:
electrically stimulating said paralyzed limb; and
actuating said stimulation in response to continuous motion of an uninvolved limb.

28. A method as recited in claim 27 wherein said muscle contraction in said paralyzed limb is induced at a rate which is related to a rate of movement of said uninvolved limb.

29. A method as recited in claim 27 where said muscle contraction in said paralyzed limb is induced at a rate which is proportional to a rate of movement of said uninvolved limb.

30. A method as recited in claim 27 wherein said actuating said stimulation in response to continuous motion of an uninvolved limb comprises:
   moving said uninvolved limb; and
   sensing a position of said uninvolved limb and transmitting a position signal indicative of said position.

31. A method as recited in claim 30 wherein said electrical stimulation of said paralyzed limb comprises:
   receiving and processing said position signal and transmitting a neuromuscular stimulation signal in response thereto; and
   transmitting said neuromuscular stimulation signal to predetermined paralyzed muscles via a plurality of electrodes to induce contraction of said paralyzed muscles of said paralyzed limb.

32. A method as recited in claim 30 wherein said sensing position of said uninvolved limb is accomplished by an electronic sensing device.

33. A method for transporting a person having a paralyzed limb, comprising:
   electrical stimulation of said paralyzed limb;
   actuating said stimulation in response to continuous motion of an uninvolved limb; and
   propelling an apparatus using said paralyzed limb.

34. A method as recited in claim 33 wherein said apparatus is propelled at a rate which is related to a rate of movement of said uninvolved limb.

35. A method as recited in claim 33 wherein said apparatus is propelled at a rate which is proportional to a rate of movement of said involved limb.

36. A method as recited in claim 33 wherein said actuating said stimulation in response to continuous motion of an uninvolved limb comprises:
   moving said uninvolved limb; and
   sensing a position of said uninvolved limb and transmitting a position signal indicative of said position.

37. A method as recited in claim 36 wherein said electrical stimulation of said paralyzed limb comprises:
   receiving and processing said position signal and transmitting a neuromuscular stimulation signal in response thereto; and
   transmitting said neuromuscular stimulation signal via a plurality of electrodes to a paralyzed muscle to induce contraction of said paralyzed muscle of said paralyzed limb.

38. A method as recited in claim 36 wherein said sensing a position of said uninvolved limb and transmitting of said position signal indicative of said position is accomplished by a mechanical cam sensing device.

39. A method as recited in claim 36 wherein said sensing a position of said uninvolved limb and transmitting of said position signal indicative of said position is accomplished by an electronic sensing device.

40. A method for inducing muscle contraction in a paralyzed limb, comprising:
   electrically stimulating said paralyzed limb; and
   energizing said stimulation only during a time that an uninvolved limb is in continuous motion.

41. A method for inducing muscle contraction in a paralyzed limb, comprising:
   electrically stimulating said paralyzed limb; and
   actuating said stimulation only during a time that an uninvolved limb is in motion.

42. Apparatus for transporting a person having a paralyzed limb, comprising:
   means for electrical stimulation of said paralyzed limb;
   means for actuating said stimulation means in response to continuous motion of an uninvolved limb; and
   means for propelling said apparatus using both said uninvolved and paralyzed limbs.

43. A method for transporting a person having a paralyzed limb, comprising:
   electrical stimulation of said paralyzed limb;
   actuating said stimulation in response to continuous motions of an uninvolved limb;
   propelling an apparatus using both the uninvolved and paralyzed limb.

* * * * *